(12) United States Patent
Woods

(10) Patent No.: US 8,585,758 B2
(45) Date of Patent: Nov. 19, 2013

(54) ACCOMMODATING INTRAOCULAR LENSES

(75) Inventor: Randall L Woods, Prescott, AZ (US)

(73) Assignee: Abbott Medical Optics Inc., Santa Ana, CA (US)

( * ) Notice: Subject to any disclaimer, the term of this patent is extended or adjusted under 35 U.S.C. 154(b) by 571 days.

(21) Appl. No.: 12/700,449

(22) Filed: Feb. 4, 2010

(65) Prior Publication Data
US 2011/0035001 A1 Feb. 10, 2011

Related U.S. Application Data

(63) Continuation of application No. 10/280,918, filed on Oct. 25, 2002, now abandoned.

(51) Int. Cl.
*A61F 2/16* (2006.01)

(52) U.S. Cl.
USPC .................. 623/6.37; 623/6.38; 623/6.39

(58) Field of Classification Search
USPC .............. 623/6.24, 6.32, 6.37–6.4, 6.43
See application file for complete search history.

(56) References Cited

U.S. PATENT DOCUMENTS

| | | | |
|---|---|---|---|
| 1,483,509 A | 5/1921 | Bugbee |
| 2,129,305 A | 9/1938 | William |
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley |
| 3,227,507 A | 1/1966 | William |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |

(Continued)

FOREIGN PATENT DOCUMENTS

| AU | 3225789 A1 | 10/1989 |
|---|---|---|
| CH | 681687 A5 | 5/1993 |

(Continued)

OTHER PUBLICATIONS

Amo Specs Model AC-21B, 1992.

(Continued)

*Primary Examiner* — David H Willse
*Assistant Examiner* — Javier Blanco
(74) *Attorney, Agent, or Firm* — Abbott Medical Optics Inc.

(57) ABSTRACT

An intraocular lens having a light-transmitting optic (32, 94*a*, 94*b*, 142, 216) comprised of a synthetic light-refractive material (40, 102) operably coupled with a flexible optic positioning member (34, 62, 74, 84, 100, 210) to refract light onto the retina in order to correct refractive errors in the eye (10). The refractive material has an index of refraction of from about 1.36 to 1.5 or higher. The optic positioning member (34, 62, 74, 84, 100, 210) is constructed of a flexible synthetic resin material such as polymethylmethacrylate and permits focusing upon objects located near to and far from the viewer. The optic (32, 94*a*, 94*b*, 142, 216) of the present invention possess greater refractive capability than optics conventionally used in IOL construction, and permits retinal receipt of the image being viewed in order to correct refractive errors.

4 Claims, 6 Drawing Sheets

(56) References Cited

U.S. PATENT DOCUMENTS

| | | |
|---|---|---|
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,794,414 A | 2/1974 | Wesley |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | De Carle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider et al. |
| 5,201,762 A | 4/1993 | Hauber |
| 5,225,858 A | 7/1993 | Portney |
| 5,258,025 A | 11/1993 | Fedorov et al. |

(56) References Cited

U.S. PATENT DOCUMENTS

| | | | |
|---|---|---|---|
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,988 E | 7/1995 | Yang et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,876,442 A | 3/1999 | Lipshitz et al. |
| 5,898,473 A | 4/1999 | Seidner et al. |
| 5,968,094 A | 10/1999 | Werblin et al. |
| 5,984,962 A | 11/1999 | Anello et al. |
| 6,013,101 A | 1/2000 | Israel |
| 6,051,024 A | 4/2000 | Cumming |
| 6,083,261 A | 7/2000 | Callahan et al. |
| 6,096,078 A | 8/2000 | McDonald |
| 6,110,202 A | 8/2000 | Barraquer et al. |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,176,878 B1 | 1/2001 | Gwon et al. |
| 6,197,058 B1 | 3/2001 | Portney |
| 6,197,059 B1 | 3/2001 | Cumming |
| 6,200,342 B1 | 3/2001 | Tassignon |
| 6,217,612 B1 | 4/2001 | Woods |
| 6,231,603 B1 | 5/2001 | Lang et al. |
| 6,299,641 B1 | 10/2001 | Woods |
| 6,302,911 B1 | 10/2001 | Hanna |
| 6,322,589 B1 | 11/2001 | Cumming |
| 6,399,734 B1 | 6/2002 | Hodd et al. |
| 6,406,494 B1 | 6/2002 | Laguette et al. |
| 6,443,985 B1 | 9/2002 | Woods |
| 6,485,516 B2 | 11/2002 | Boehm |
| 6,488,708 B2 | 12/2002 | Sarfarazi |
| 6,503,276 B2 | 1/2003 | Lang et al. |
| 6,524,340 B2 | 2/2003 | Israel |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,592,621 B1 | 7/2003 | Domino |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,749,633 B1 | 6/2004 | Lorenzo et al. |
| 6,749,634 B2 | 6/2004 | Hanna |
| 6,855,164 B2 | 2/2005 | Glazier |
| 6,930,838 B2 | 8/2005 | Schachar |
| 7,018,409 B2 | 3/2006 | Glick et al. |
| 7,025,783 B2 | 4/2006 | Brady et al. |
| 7,097,660 B2 | 8/2006 | Portney |
| 7,125,422 B2 | 10/2006 | Woods et al. |
| 7,150,759 B2 | 12/2006 | Paul et al. |
| 7,179,292 B2 | 2/2007 | Worst et al. |
| 7,220,279 B2 | 5/2007 | Nun |
| 7,223,288 B2 | 5/2007 | Zhang et al. |
| 7,503,938 B2 | 3/2009 | Phillips |
| 7,815,678 B2 | 10/2010 | Ben Nun |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0188351 A1 | 12/2002 | Laguette |
| 2003/0004569 A1 | 1/2003 | Haefliger |
| 2003/0060878 A1 | 3/2003 | Shadduck |
| 2003/0060881 A1 | 3/2003 | Glick et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0187505 A1 | 10/2003 | Liao |
| 2003/0204254 A1 | 10/2003 | Peng et al. |
| 2003/0204255 A1 | 10/2003 | Peng et al. |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0111153 A1 | 6/2004 | Woods et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2005/0018504 A1 | 1/2005 | Marinelli et al. |
| 2005/0021139 A1 | 1/2005 | Shadduck |
| 2005/0027354 A1 | 2/2005 | Brady et al. |
| 2005/0085906 A1 | 4/2005 | Hanna |
| 2005/0085907 A1 | 4/2005 | Hanna |
| 2005/0125057 A1 | 6/2005 | Cumming |
| 2005/0131535 A1 | 6/2005 | Woods |
| 2005/0137703 A1 | 6/2005 | Chen |
| 2005/0288785 A1 | 12/2005 | Portney et al. |
| 2006/0064162 A1 | 3/2006 | Klima |
| 2006/0111776 A1 | 5/2006 | Glick et al. |
| 2006/0116765 A1 | 6/2006 | Blake et al. |
| 2006/0238702 A1 | 10/2006 | Glick et al. |
| 2007/0067872 A1 | 3/2007 | Mittendorf et al. |
| 2007/0078515 A1 | 4/2007 | Brady |
| 2007/0100444 A1 | 5/2007 | Brady et al. |
| 2007/0106381 A1 | 5/2007 | Blake |
| 2007/0123591 A1 | 5/2007 | Kuppuswamy et al. |
| 2007/0129798 A1 | 6/2007 | Chawdhary |
| 2007/0135915 A1 | 6/2007 | Klima |
| 2007/0213817 A1 | 9/2007 | Esch et al. |
| 2007/0260309 A1 | 11/2007 | Richardson |
| 2007/0299487 A1 | 12/2007 | Shadduck |
| 2008/0161913 A1 | 7/2008 | Brady et al. |
| 2008/0161914 A1 | 7/2008 | Brady et al. |
| 2009/0012609 A1 | 1/2009 | Geraghty et al. |

FOREIGN PATENT DOCUMENTS

| | | |
|---|---|---|
| DE | 2702117 A1 | 7/1978 |
| DE | 3246306 A1 | 6/1984 |
| DE | 4038088 A1 | 6/1992 |
| DE | 19501444 A1 | 7/1996 |
| EP | 64812 A2 | 11/1982 |
| EP | 246216 A2 | 11/1987 |
| EP | 328117 A2 | 8/1989 |
| EP | 329981 A1 | 8/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 488835 A1 | 6/1992 |
| EP | 507292 A1 | 10/1992 |

(56) References Cited

FOREIGN PATENT DOCUMENTS

| | | |
|---|---|---|
| EP | 566170 A1 | 10/1993 |
| EP | 601845 A1 | 6/1994 |
| EP | 691109 A1 | 1/1996 |
| EP | 766540 A1 | 4/1997 |
| EP | 897702 A2 | 2/1999 |
| EP | 766540 B1 | 8/1999 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 2126847 | 5/1990 |
| WO | WO8603961 A1 | 7/1986 |
| WO | WO8700299 A1 | 1/1987 |
| WO | WO8707496 A1 | 12/1987 |
| WO | WO8902251 A1 | 3/1989 |
| WO | WO8911672 A1 | 11/1989 |
| WO | WO9000889 A1 | 2/1990 |
| WO | WO9305733 A1 | 4/1993 |
| WO | WO9416648 A1 | 8/1994 |
| WO | WO9503783 A1 | 2/1995 |
| WO | WO9610968 A1 | 4/1996 |
| WO | WO9615734 A2 | 5/1996 |
| WO | WO9625126 A1 | 8/1996 |
| WO | WO9712272 A1 | 4/1997 |
| WO | WO9727825 A1 | 8/1997 |
| WO | WO9743984 A1 | 11/1997 |
| WO | WO9856315 A1 | 12/1998 |
| WO | WO0027315 A1 | 5/2000 |
| WO | WO0061036 A1 | 10/2000 |
| WO | WO0066039 A1 | 11/2000 |
| WO | WO0119288 A1 | 3/2001 |
| WO | WO0119289 A1 | 3/2001 |
| WO | WO0134066 A1 | 5/2001 |
| WO | WO0134067 A1 | 5/2001 |
| WO | WO0166042 A1 | 9/2001 |
| WO | WO0219949 A2 | 3/2002 |
| WO | WO03015669 A1 | 2/2003 |
| WO | WO03034949 A2 | 5/2003 |
| WO | WO03059208 A2 | 7/2003 |
| WO | WO03075810 A1 | 9/2003 |
| WO | WO2005018504 A1 | 3/2005 |
| WO | WO2005115278 A1 | 12/2005 |
| WO | WO2007040964 A1 | 4/2007 |
| WO | WO2007067872 A2 | 6/2007 |
| ZA | 0888414 | 11/1988 |

OTHER PUBLICATIONS

"DVD titled "New elliptical accommodative IOL for cataract surgery" shown at ASCRS Symposium on Apr. 10, 1999.,".
English translation of Payer CH 681 687.
European Search Report for Application No. EP09178394, mailed on Jan. 25, 2010, 2 pages.
Fechner P.U., et al., "Iris-Claw Lens In Phakic Eyes To Correct Hyperopia: Preliminary Study," Journal of Cataract and Refractive Surgery, 1998, vol. 24 (1), pp. 48-56.
International Search Report for Application No. PCT/US2003/34163, mailed on Apr. 12, 2004, 1 page.
"Mandell, Contact Lens Practice, 4 th Ed,".
Menezo J.L., et al., "Endothelial Study of Iris-Claw Phakic Lens: Four Year Follow-Up," Journal of Cataract Refractive Surgery, 1998, vol. 24 (8), pp. 1039-1049.
"Program from ASCRS Symposium showing video tape between Apr. 10-14, 1999, 2 pages.,".
"Study Design of Nuvita, Mar. 20, 1997, 5 pages,".
Supplementary European Search Report of EP Patent Application No. EP03809651, dated Aug. 11, 2006, 2 pages total.
U.S. Appl No. 10/280,918, filed Aug. 5, 2003.
U.S. Appl No. 10/280,937, filed Oct. 25, 2005.
English translation of WO 93/05733A1.
U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.

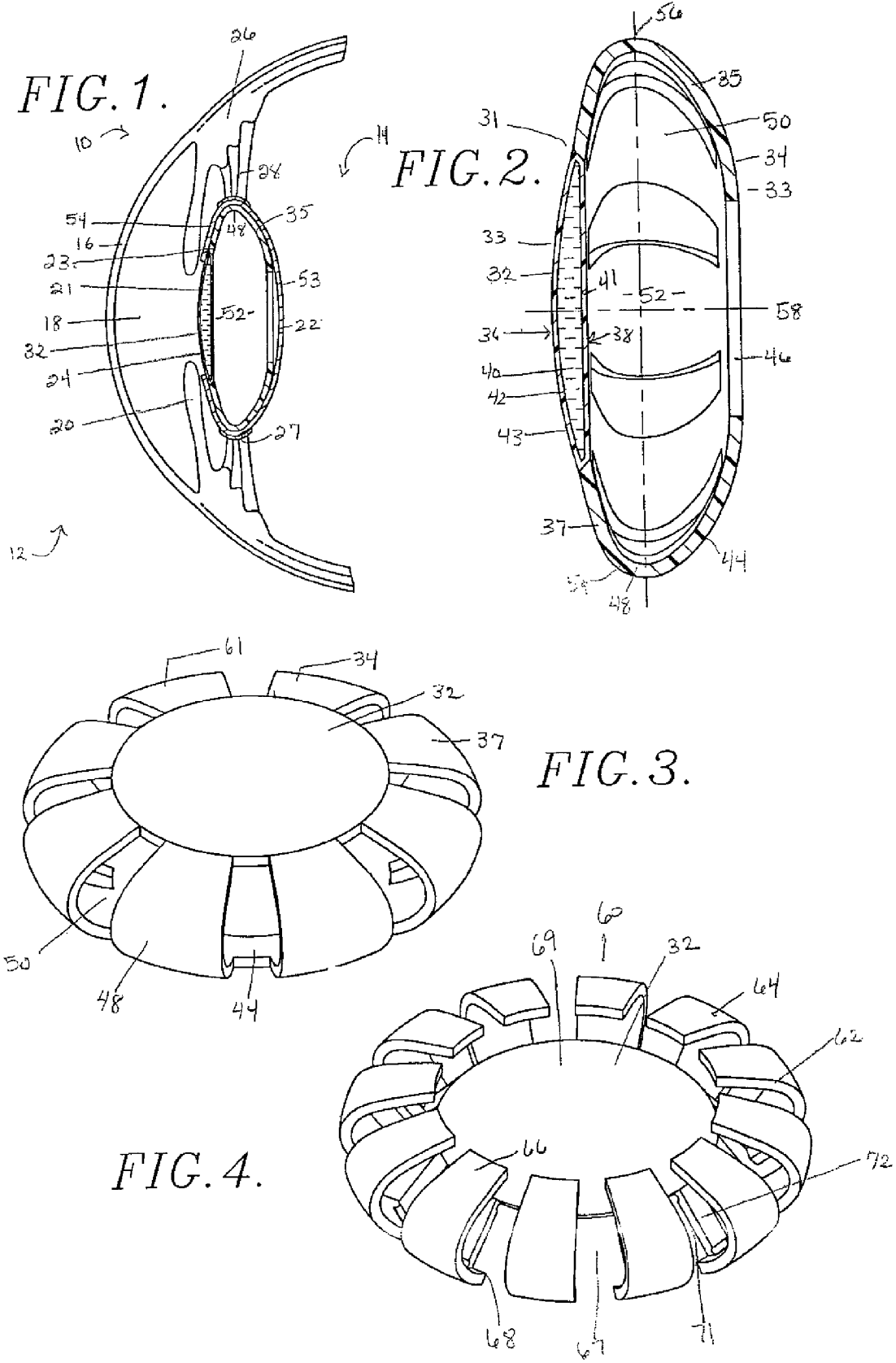

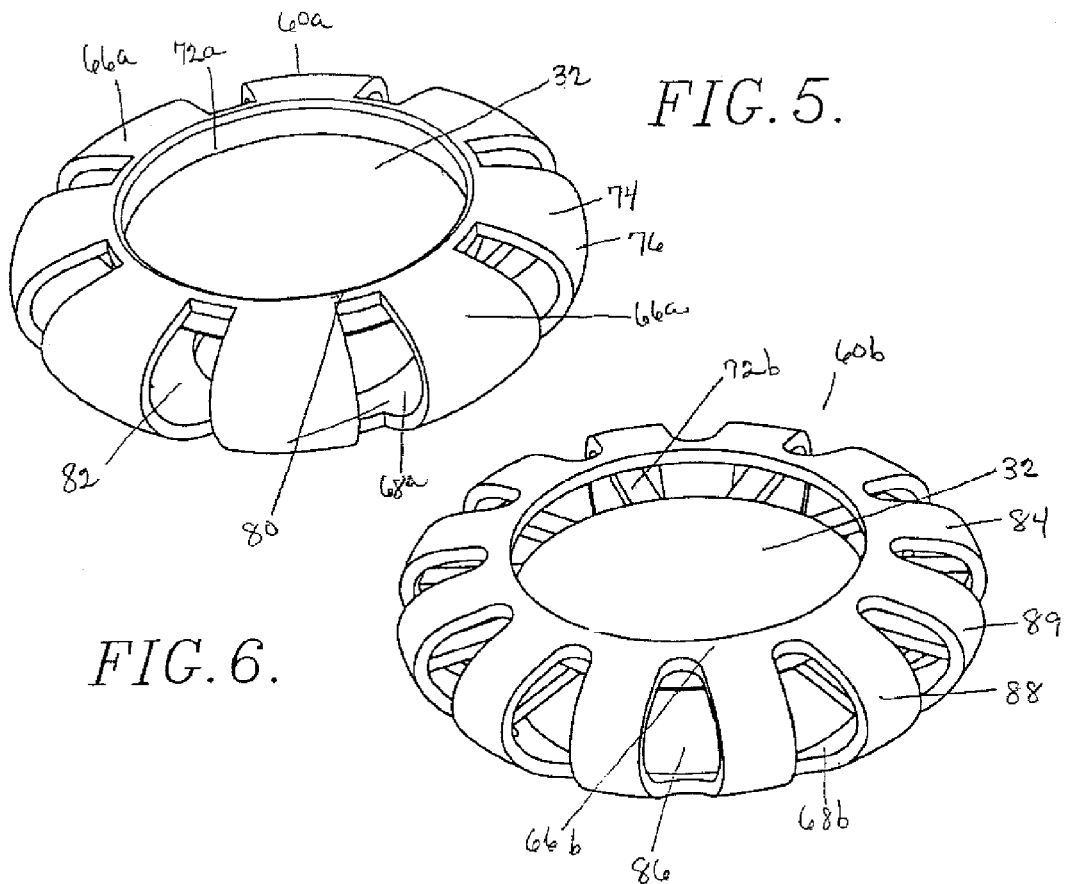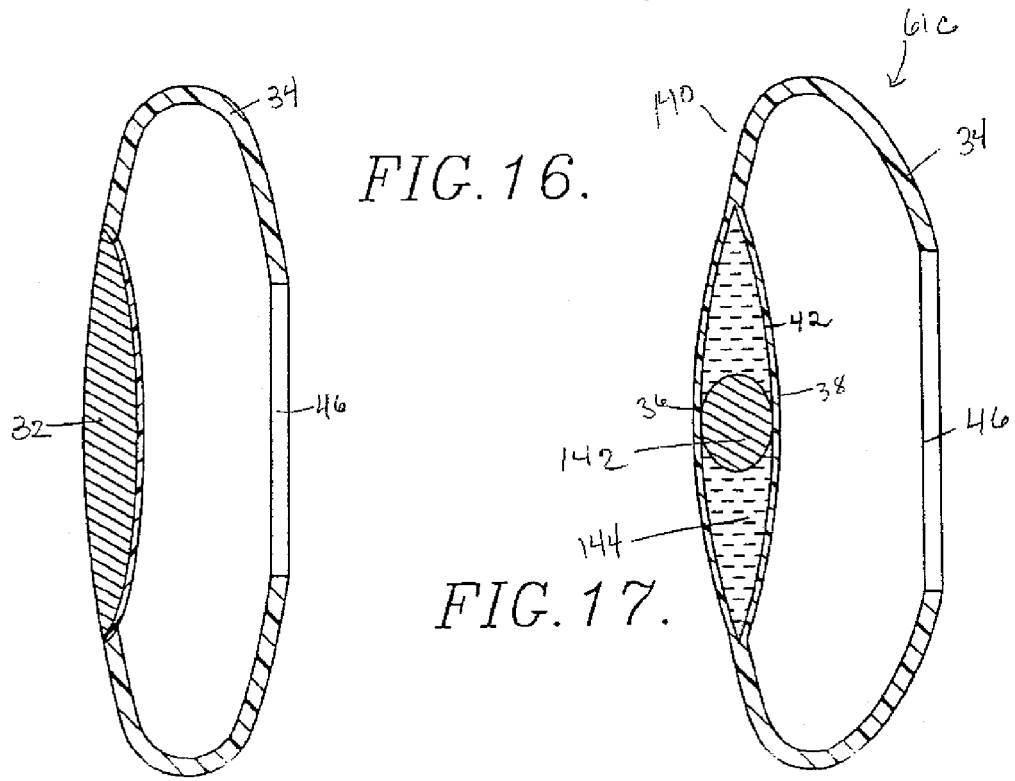

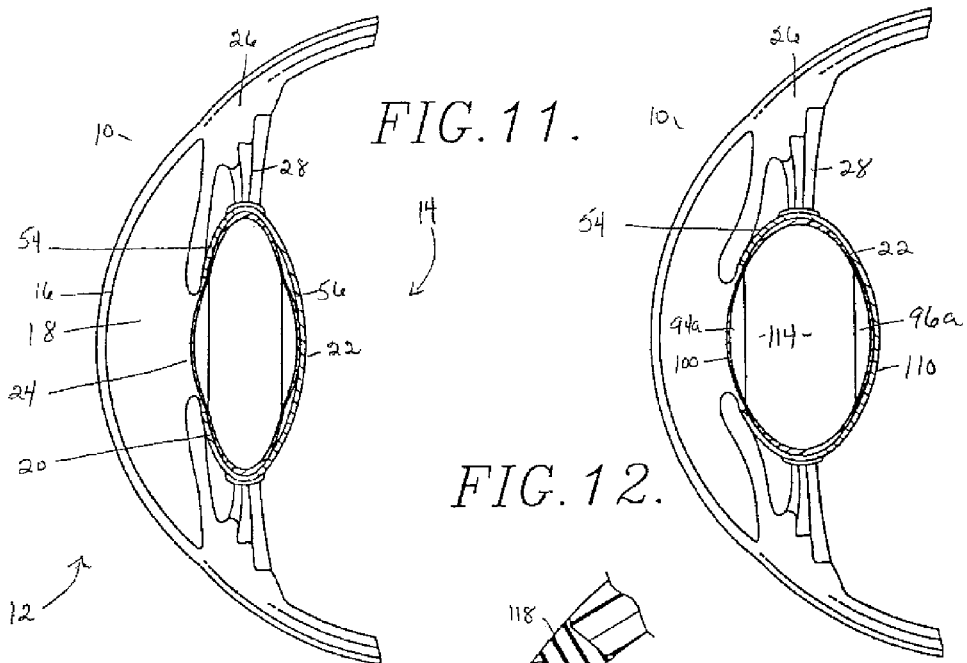
FIG. 11.
FIG. 12.
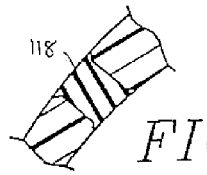
FIG. 15.
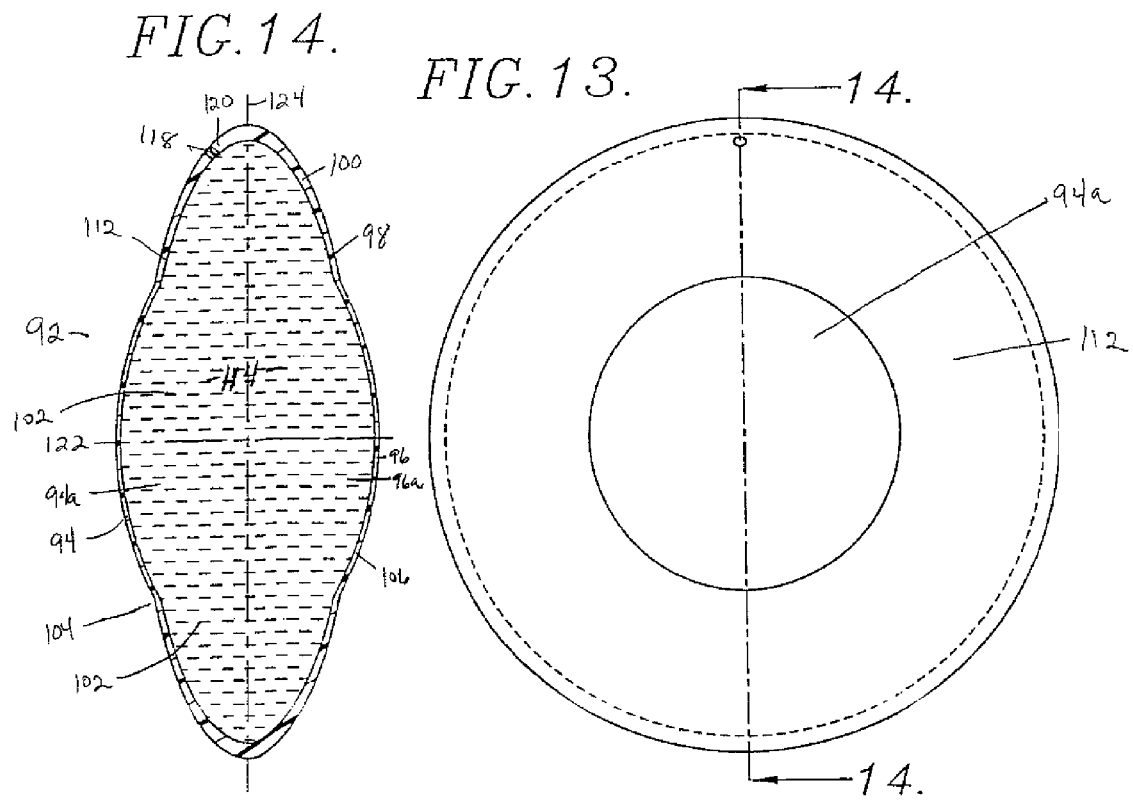
FIG. 14.
FIG. 13.

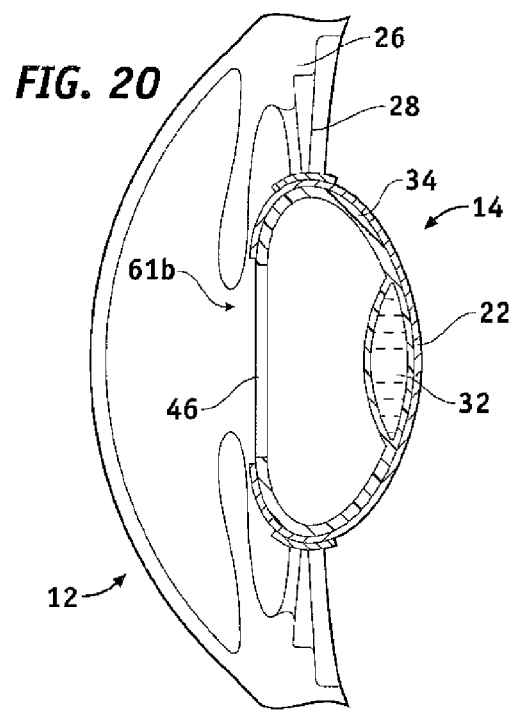
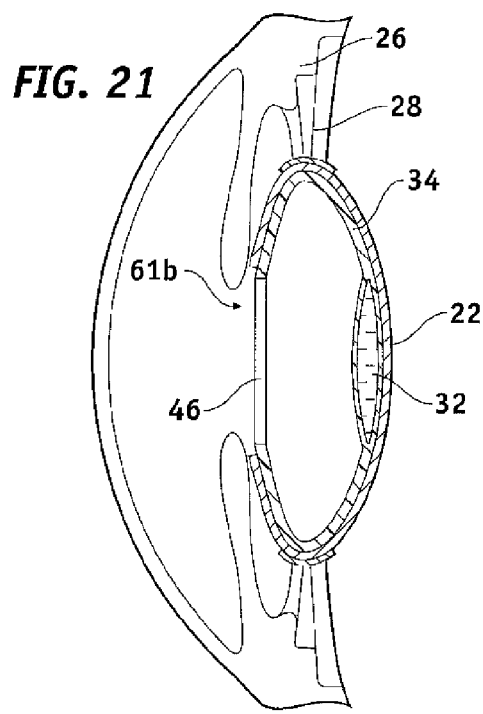
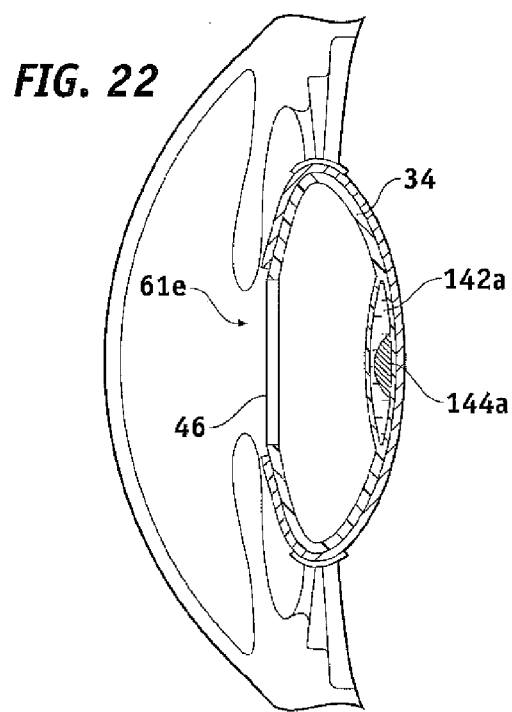

ACCOMMODATING INTRAOCULAR LENSES

RELATED APPLICATION

The present application is a continuation application of, and claims priority to, U.S. patent application Ser. No. 10/280,918, filed Oct. 25, 2002, now abandoned, which application is hereby incorporated by reference in it entirety for all purposes as if fully set forth herein.

BACKGROUND OF THE INVENTION

1. Field of the Invention

The present invention relates to an accommodating intraocular lens implant (IOL), containing a refractive material therein, for surgical replacement of the natural crystalline lens to treat refractive errors in the human eye.

2. Description of the Prior Art

Refractive errors in the eye affect one's ability to properly focus an image upon the retina due to a change in the refractive medium of the eye, e.g., the cornea, the natural crystalline lens, or both. The refractive errors pertinent to this application include myopia, hyperopia, and presbyopia. A myopic lacks the ability to focus an image located at a distance from the viewer because the cornea has become elongated, thereby increasing the eye's focal length. A hyperopic lacks the ability to focus on objects located near the viewer because the cornea is not elongated enough or is too flat, and cannot refract light properly upon the retina. Instead, light entering the eye does not bend sharply enough to focus upon the retina. In contrast to myopia wherein the image is brought to focus in front of the retina, hyperopia causes the image to focus behind the retina. Presbyopia is another type of refractive error which results in the inability of the eye to focus because of hardening of the natural crystalline lens. The hardened natural crystalline lens prevents focusing upon objects located near to the viewer. Presbyopia occurs in conjunction with myopia or hyperopia.

The known treatment varies with the type of refractive error to be corrected. Each of the refractive errors may be corrected by external spectacle lenses. Also, refractive surgery is known in the art for correcting the aforementioned refractive errors, and includes radial keratotomy, astigmatic keratotomy, photoreflective keratectomy, and laser in situ keratomileusis (LASIK). Each of the refractive surgical methods mentioned above involve making multiple incisions into the cornea in order to reshape it. Possible side effects of refractive surgery include irregular astigmatism, infection, or haze formation which could result in permanent changes in the cornea and possible loss of best-corrected visual acuity. A possibility of under or over correction also exists with the aforementioned refractive surgeries. Furthermore, none of these refractive surgeries can be used to correct all of the above-referenced refractive errors.

Various IOLs have been used to treat cataracts. The first implant of an IOL within the eye to treat cataracts occurred in 1949. This experimental surgery attempted to place the replacement lens in the posterior chamber of the eye behind the iris. Problems such as dislocation after implantation forced abandonment of this approach, and for some period thereafter IOLs were implanted in the anterior chamber of the eye.

Others returned to the practice of inserting the IOL in the area of the eye posterior to the iris, known as the posterior chamber. This is the area where the patient's natural crystalline lens is located. When the IOL is located in this natural location, substantially normal vision may be restored to the patient, and the problems of forward displacement of the vitreous humor and retinal detachment encountered in anterior chamber IOLs are less likely to occur. IOLs implanted in the posterior chamber are disclosed in U.S. Pat. Nos. 3,718,870, 3,866,249, 3,913,148, 3,925,825, 4,014,049, 4,041,552, 4,053,953, and 4,285,072. None of these IOLs have accommodation capability.

IOLs capable of focusing offered the wearer the closest possible substitute to the natural crystalline lens. U.S. Pat. No. 4,254,509 to Tennant discloses an IOL which moves in an anterior direction upon contraction of the ciliary body and which is located anterior to the iris. Although the Tennant IOL claims to possess accommodation capabilities, it presents the same disadvantages as other anterior chamber lenses. U.S. Pat. No. 4,253,199 to Banko approaches the problem of providing a focusable IOL in a different manner, by providing a replacement IOL of deformable material sutured to the ciliary body. This IOL functions in much the same manner as the natural crystalline lens, but may cause bleeding because it requires sutures.

U.S. Pat. No. 4,409,691 to Levy claims to provide an accommodating IOL positioned within the capsule. This IOL is located in the posterior area of the capsule and is biased toward the fovea or rear of the eye. The Levy IOL is deficient because it requires the ciliary muscle to exert force through the zonules on the capsule in order to compress the haptics inward and drive the optic forward for near vision. However, the ciliary muscles do not exert any force during contraction because the zonules, being flexible filaments, exert only tension, not compression on the capsule. The natural elasticity of the IOL causes the capsule to become more spherical upon contraction of the ciliary muscle. Thus, there is no inward force exerted on the capsule to compress the haptics of the Levy IOL, and therefore accommodate for near vision. Even if such force were somehow available, the Levy IOL's haptics are loaded inward when accommodating for near vision. Since accommodation for near vision is the normal status of the capsule, the Levy IOL's haptics are loaded, reducing the fatigue life of the springlike haptics.

U.S. Pat. No. 5,674,282 to Cumming is directed towards an allegedly accommodating IOL for implanting within the capsule of an eye. The Cumming IOL comprises a central optic and two plate haptics which extend radially outward from diametrically opposite sides of the optic and are movable anteriorly and posteriorly relative to the optic. However, the Cumming IOL suffers from the same shortcomings as the Levy IOL in that the haptics are biased anteriorly by pressure from the ciliary bodies. This will eventually lead to pressure necrosis of the ciliary body.

Finally, U.S. Pat. No. 4,842,601 to Smith discloses an allegedly accommodating IOL having anterior and posterior members which urge against the anterior and posterior walls of the capsule. The muscular action exerted on the capsule will cause the IOL to flatten, thereby changing the focus thereof. The Smith IOL is formed of first and second plastic lens members connected to one another adjacent their peripheral edges so as to provide a cavity therebetween. The connection between the lens members is accomplished by way of a U-shaped flange on the first member which forms an inwardly facing groove for receiving an outwardly extended flange on the second member. The Smith IOL is faulty because the structure of the lens members makes surgical implantation thereof extremely difficult to accomplish, even for highly skilled surgeons. Furthermore, the Smith IOL requires sutures which increases the risk of bleeding.

The IOLs discussed above replaced the opaque crystalline lens symptomatic of cataracts through a small incision in the iris and anterior wall of the biological capsule. The IOLs for the treatment of cataracts differed from the present invention in that the present invention utilizes a highly refractive material to compensate for defects in the eye's natural refractive media, e.g, the cornea and the natural crystalline lens.

There is a great need in the art for a lightweight IOL which can be used to correct a variety of refractive errors in conjunction with other eye defects which require replacement of the natural crystalline lens, such as cataracts. This IOL should be readily insertable into the capsule and should last for a substantial number of years without damaging any of the eye components.

SUMMARY OF THE INVENTION

The IOL of the present invention addresses this need because it provides a lightweight accommodating IOL, containing a highly refractive material therein, which is safe for long term use in an eye. The present invention presents a significant advance in the art because it provides an IOL for the safe and effective treatment of refractive errors in combination with other defects such as cataracts.

In more detail, the IOL comprises a resilient optic formed of a highly refractive material operably coupled to a flexible optic positioning member to change shape in response to ciliary body movement, i.e., contraction and retraction of the ciliary body. When the ciliary body relaxes or retracts, it causes the zonules to elongate and exert a tensional pull upon the IOL. Thus, the IOL becomes discoid in shape and allows the viewer to focus upon objects located at a distant therefrom. Similarly, when the ciliary body contracts, it becomes thicker and causes the zonules to ease the tensional pull. Thus, the IOL becomes spheroid in shape and allows the viewer to focus upon objects located near to the viewer. As noted above, the optic is formed of refractive material that has an index of refraction of from about 1.36 to 1.5 or higher (e.g., hydrocarbon oil, silicone oil, or silicone gel). In one type of IOL in accordance with the invention, use is made of a pre-formed capsule having a thin, continuous wall wherein the refractive material is enveloped.

The optic may be coupled with various optic positioning members commonly used in IOL construction depending upon the user's eyesight. The optic may be positioned within the capsule of the eye such that the anterior surface of the optic faces either the anterior or the posterior portion of the eye. When the optic is positioned to face the posterior portion of the eye, the optic will vault posteriorly in response to contraction of the ciliary body. However, the change in the radius of curvature of the optic will counteract the effects of the negative accommodation, i.e., movement of the optic posteriorly. The resiliency of the optic permits a small change in radius of curvature which, when coupled with the relatively high index of refraction of the refractive material, results in an optic having greater light-bending properties than conventional optics.

Another preferred embodiment presents a resilient optic and a posterior rigid optic both operably coupled on opposed sides of an optic positioning member to change shape in response to ciliary body movement. The optics are positioned on opposite segments of the optic positioning members such that they share the same focal point. A similar embodiment transposes the structure described immediately above by implanting the IOL within the eye such that the rigid optic is the anterior optic and the resilient optic is the posterior optic.

Another embodiment of the present invention presents two optics positioned on the same segment of the optic positioning member wherein a rigid optic surrounds a resilient optic.

Another embodiment similar to the embodiment discussed immediately above, presents two optics positioned on the same segment of the optic positioning member wherein a resilient optic surrounds a rigid optic. In this embodiment, the resilient optic changes shape in response to ciliary body movement while the rigid optic essentially retains its shape.

Yet another preferred embodiment of the IOL of the present invention includes an optic positioning member comprised of an enclosed flexible bag having resilient fill material therein. The enclosed flexible bag presents an anterior segment and an opposed posterior segment, each having an optic. The optic positioning member is pre-formed to present opposed optic surfaces, hence, the optics are integral with the optic positioning member. The resilient fill material is comprised of the same refractive material used in the above-referenced resilient optic construction. This embodiment also functions similarly to the IOLs discussed above because the anterior optic surface moves anteriorly and the posterior optic surface moves posteriorly in response to contraction of the ciliary body. The optic surfaces of the flexible bag optic positioning member present a small change in the radius of curvature (e.g., 5-4.6 mm) from the accommodated to disaccommodated shapes, coupled with high refractive power thereby permitting retinal receipt of an observed image.

Another embodiment of the present invention is similar to the embodiments having opposed optics, described above, except that the optic positioning member of this embodiment does not completely house the refractive material. The refractive material of this IOL protrudes outward to extend beyond the outer margins of the anterior segment through an opening in the optic positioning member to define a resilient optic. The posterior segment of the optic positioning member supports a second posterior rigid optic positioned in opposition to the resilient optic. The rigid optic is constructed of the same material as the optic positioning member. The resilient material is captively retained by the segments of the optic positioning member, but also directly contacts the biological capsule. Contraction of the ciliary body transfers sufficient force to the resilient and protuberant refractive material which in turn defines an optic operable to change shape in response to ciliary body movement. This embodiment may be constructed without the addition of a second opposed rigid optic depending upon identifiable surgical needs.

BRIEF DESCRIPTION OF THE DRAWINGS

FIG. 1 is a vertical sectional view showing an IOL of the invention within the capsule of an eye, with the eye focused on an object distant from the viewer;

FIG. 2 is a vertical sectional view of a preferred IOL of the invention;

FIG. 3 is an anterior perspective view of the IOL of FIGS. 1 and 2;

FIG. 4 illustrates another embodiment of the invention;

FIG. 5 illustrates another embodiment of the invention;

FIG. 6 illustrates another embodiment of the invention;

FIG. 11 is a vertical sectional view of a preferred IOL of the invention within the capsule of an eye, with the eye focused on an object distant from the viewer;

FIG. 12 is a view similar to that of FIG. 11, but illustrating the IOL in an accommodated position owing to contraction of the ciliary body;

FIG. 13 is a plan view of a preferred IOL of the invention;

FIG. 14 is a vertical sectional view taken along line 14-14 of FIG. 13; and

FIG. 15 is a greatly enlarged fragmentary of the IOL of FIGS. 11-14;

FIG. 16 is a vertical sectional view similar to that of FIGS. 7-10, but illustrating the optic constructed without an enveloping capsule;

FIG. 17 is a vertical sectional view of another embodiment of the present invention, illustrating a resilient optic surrounded by a rigid optic;

FIG. 20 is a vertical sectional view showing an IOL of the invention within the capsule of an eye, with the optic positioned posteriorly;

FIG. 21 is a view similar to that of FIG. 20, but illustrating the IOL in a disaccommodated position owing to retraction of the ciliary muscle; and FIG. 22 is a vertical sectional view of another embodiment of the IOL of the present invention positioned within the capsule of the eye.

DETAILED DESCRIPTION OF THE PREFERRED EMBODIMENTS

Figure 7:
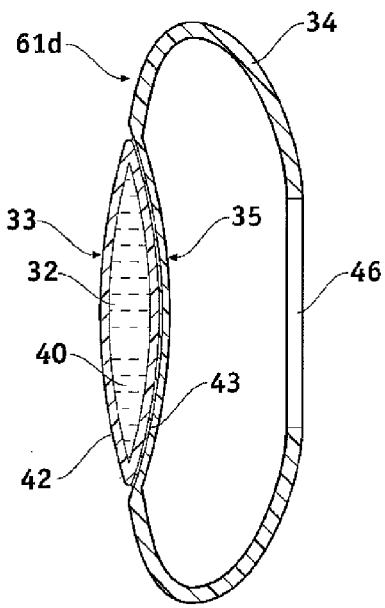
FIG. 7 is a vertical sectional view of the IOL of FIG. 3 showing the optic bonded to the anterior surface of the anterior segment of the IOL of the present invention.

Referring now to the drawings, the present invention is in the form of an IOL for surgical replacement of the natural crystalline lens in the treatment of refractive error in the human eye. FIG. 1 shows the various components of the human eye 10 pertinent to this invention. Briefly, the eye 10 includes an anterior portion 12 and a posterior portion 14. The anterior portion 12 of the eye 10 is covered by a cornea 16 which encloses and forms an anterior chamber 18. The anterior chamber 18 contains aqueous fluid and is bounded at the rear by an iris 20. The iris 20 opens and closes to admit appropriate quantities of light into the inner portions of the eye 10. The eye 10 also includes a capsule 22 which ordinarily contains the natural crystalline lens (which would be located at numeral 24 in the natural, unmodified eye). The eye 10 includes a ciliary muscle or body 26 having zonular fibers 28 (also referred to as zonules) which are attached to the eye 10. The vitreous humor 30 is located posterior to the capsule 22 and anterior to the retina (not pictured). The vitreous humor 30 contains vitreous fluid.

Most of the light entering the eye 10 is refracted at the air-cornea interface. The cornea 16 has an index of refraction of 1.37, and is largely responsible for refracting light into the eye 10. The light then slightly diverges in the fluid-filled anterior chamber 18 which has an index of refraction close to that of water, e.g., approximately 1.33, and travels to the natural crystalline lens 24. The natural crystalline lens 24 is a biconvex structure having an index of refraction of 1.4 at its center and an index of refraction of 1.38 at its outer portion. Next to the cornea 16, the natural crystalline lens 24 is responsible for refracting much of the light entering the human eye 10. The anterior portion of the natural crystalline lens 24 converges light onto its posterior portion where light is then diverged. It is at this point, that the image being viewed is inverted. The inverted image (or light) then travels into the vitreous humor 30 and through the vitreous fluid. The vitreous fluid has an index of refraction close to that of water, e.g. 1.33. After the inverted image travels through the vitreous humor 30, it is brought to focus upon the retina. The retina is responsible for relaying electric signals to the optic nerve. The optic nerve then carries the message to the brain which translates the inverted image into its upright position.

Ocular adjustments for sharp focusing of objects viewed at different distances are accomplished by the action of the ciliary body 26 on the capsule 22 and natural crystalline lens 24 through the zonules 28. The ciliary body 26 contracts, allowing the capsule 22 to return to a more spherical shape for viewing objects near to the viewer. When the ciliary body 26 retracts, to the ciliary body 26 pulls on the zonules 28 to make the capsule 22 more discoid thus permitting objects at a distance to be viewed in proper focus. (FIG. 1) To summarize, when the eye 10 focuses, the capsule 22 changes shape to appropriately distribute the light admitted through the cornea 16 and the iris 20.

Referring now to FIGS. 1-22, an IOL in accordance with the invention comprises an optic 32 operably coupled to an optic positioning member and implanted within the capsule 22 of the human eye 10. The IOL changes shape in response to ciliary body 26 movement. As previously noted, the optic 32 of the present invention is formed of a highly refractive material. The refractive material has an index of refraction of from about 1.36 to 1.5 or higher. Examples of preferred refractive materials include silicone oil, hydrocarbon oil, and more preferably silicone gel (available from Nusil Technology). When the refractive material used is a gel, the gel may be pre-formed into the desired optic shape and adhered onto the optic positioning member without encapsulating it.

The optic 32 may be utilized in a number of ways in a variety of optic positioning members. The optic positioning members discussed herein are preferably formed of any appropriate biologically inert material conventionally used in IOL construction (e.g., elastic, synthetic resin materials). Examples of suitable materials include acrylates (such as polymethylmethacrylates), silicones, and mixtures of acrylates and silicones. It is contemplated that mixtures of silicones and acrylates comprise both chemical mixtures, such as silicone-acrylate blends, and various combinations of silicones and acrylates employed to construct the lens. It is particularly preferred that the optic positioning members according to the invention be constructed of a material having an elastic memory (i.e., the material should be capable of substantially recovering its original size and shape after a deforming force has been removed). An example of a preferred material having elastic memory is MEMORYLENS (available from Mentor Ophthalmics in California).

The preferred embodiments of the IOL of the instant invention discussed immediately below demonstrate the variety of optic positioning members that may be operably coupled with the inventive optic to correct refractive errors in the eye. The terms rigid optic and resilient optic are used herein as relative terms to one another. For instance, a rigid optic may be any optic that is less resilient than the resilient optic of the present invention, even though the rigid optic may be more resilient than another rigid optic. The optics of the present invention may be made of varying degrees of resiliency and rigidity depending upon the materials used, therefore, the terms rigid and resilient should not be used as limiting terms other than to convey a specific relationship between two optics within the scope of this invention.

The IOL of FIGS. 1-3 [IOL 61]

The optic 32 presents a convex anterior surface 36 and a planar posterior surface 38 (hereinafter plano-convex). Although the optic 32 is illustrated as plano-convex, the size and shape of the optic 32 may be varied depending upon the user's eyesight. The optic 32 is composed of a refractive material 40 that is enveloped within a pre-formed capsule 42 formed of a thin continuous wall 43 made of the same flexible synthetic resin material as the optic positioning member 34. The thin wall 43 has an anterior section 33 facing the anterior portion 12 of the eye 10 and a posterior section 41 facing the posterior portion 14 of the eye 10 respectively. (See FIG. 2) The anterior section 33 of the thin wall 43 has a thickness of from about 0.0005 to 0.025 mm, and more preferably of about 0.004 mm, when the material used is silicone. The posterior section 41 of the thin wall 43 has a thickness of from about 0.0005 to 0.025 mm, and more preferably of about 0.003 mm, when the material used is silicone. One of ordinary skill in the art will appreciate that the anterior section 33 and the posterior section 41 of the thin wall 43 may also be constructed of uniform thickness. The optic 32 may also be constructed without the refractive material housed within the pre-formed capsule 42 when the refractive material used is the silicone gel material discussed above. (See FIG. 16)

The optic positioning member 34 may be integral with optic 32 or may be structurally distinct. As illustrated, the optic positioning member 34 comprises a main body 35 which includes an annular posterior segment 44 with a central opening 46 and an anterior segment 37. Anterior segment 37 and posterior segment 44 are located on either side of equatorial axis 56. A plurality of circumferentially spaced, arcuate in cross-section positioning legs 48 extend from the segment 44 and are joined to the margin of optic 32, with openings 50 defined between adjacent pairs of the legs 48. As perhaps best seen in FIG. 2, the legs 48 cooperatively present, with the optic 32, a substantially discoid shape with a central chamber 52. However, the legs 48 also define an annular equatorial segment 54 disposed on opposite sides of equatorial axis 56. (See FIG. 2) The overall IOL 61 further presents a central polar axis 58 as shown. Preferably, the outside dimension of the IOL 61 at the equatorial segment 48 is from about 8 to 12 mm. On the other hand, the outside dimension along polar axis 58 is typically from about 1 to 5 mm. These dimensions given immediately above, however, are only representative of some typical dimensions within the ambit of the present invention. A wide range of variance necessarily exists for the dimensions of the IOLs of this invention because a wide degree of biological variance exists. Clearly, the dimensions of the IOLs of the present invention must conform to the size and shape of the eye to be fitted. One of ordinary skill in the art will readily appreciate this.

The optic positioning member 34 discussed herein is configured so as to substantially conform with the capsule 22, particularly to the equatorial portion 27 of the capsule 22. This is shown in FIGS. 1 and 2 where it will be observed that the equatorial segment 54 of the IOL 61 is in substantially conforming contact with the inner surface of the equatorial portion 27 of capsule 22. This close conforming relationship is maintained notwithstanding the extent of accommodation of IOL 61.

IOL 61 is inserted into the human eye 10 in the following manner. An ophthalmic surgeon would remove the natural crystalline lens 24 by conventional methods, leaving an opening 21 in the anterior wall 23 of the capsule 22. IOL 61 is then folded into a compact size for insertion in the capsule 22 through opening 21. Once inserted, the capsule 22 is filled with fluids (e.g., saline solution) which enter the IOL 61 causing IOL 61 to return to its original, non-deformed state as shown in FIG. 1. There is no need to suture the IOL 61 to the capsule 22 because, due to the size and shape of IOL 61 and conformance of the IOL 61 to the capsule 22, the IOL 61 will not rotate or shift within the capsule 22.

Optionally, IOL 61 may be provided with a very thin membrane (not shown) in covering relationship as disclosed in U.S. patent application Ser. No. 09/940,018, filed Aug. 27, 2001, which is incorporated by reference herein. It is contemplated that the membrane would be formed of the same synthetic resin as the optic positioning member 34 but would be much thinner (on the order of a few thousandths of an inch) than the remainder of the optic positioning member 34. The purpose of the membrane is to prevent or at least impede the passage of migratory cells through openings within the IOL 61 and into the inner chamber of the IOL 61.

Furthermore, optic positioning member 34 construction is disclosed in previously filed application for U.S. patent Ser. No. 10/280,937 entitled Accommodating Intraocular Lens Implant and U.S. patent Ser. No. 09/940,018 entitled Intraocular Lens Implant Having Eye Accommodating Capabilities both to the same applicant, which are hereby incorporated by reference herein as is necessary for a full and complete understanding of the present invention.

Implantation of the inventive IOL 61 restores normal vision by providing an optic 32 formed of highly refractive material capable of bending light onto the retina. After implantation of the IOL 61 in the human eye 10, light refracts at the air-cornea interface in the same manner as the natural human eye 10. The light travels through the fluid-filled anterior chamber 18 and onto the optic 32. The radius of curvature of the optic 32 changes in response to ciliary body 26 movement, thus affecting the optic's 32 refractive capabilities.

Not only does the IOL 61 project an observed image onto the retina, but it also accommodates in response to action of the ciliary body 26 in connection with the zonules 28 to view objects located both near and far from the viewer. When the viewer is observing an image located at a distance, the sensory cells within the retina signal the ciliary body 26 to relax, thus pulling on the zonules 28 to make the capsule 22 more discoid as shown in FIG. 1. In doing so, the polar dimension of the capsule 22 narrows, subsequently causing the polar dimension of the IOL 61 to similarly narrow. Those ordinarily skilled in the art will appreciate that the optic positioning member 34 is operably coupled with the optic 32 of the present invention to change shape in response to ciliary body 26 movement. In this regard, the movement of the ciliary body 26 causes the optic 32 to move posteriorly and anteriorly, respectively. Contraction of the ciliary body 26 and subsequent relaxation of the zonules 28 will cause the optic 32 to vault anteriorly.

The IOL 61 of the present invention typically has a diopter value of from about 16 to 26. The diopter value of a lens is defined as the reciprocal of the focal length in meters:

$$\text{Diopter} = 1/\text{focal length (m)}$$

Focal length is the distance from the center of the lens to the object being viewed. The focal length must decrease as magnification increases. The diopter value expresses the refractive capacity of a lens which is associated with the radius of curvature of the optics. Generally, an increased diopter value indicates that the optic is thicker and also has a lesser radius of curvature thus possessing greater light-bending capability.

The IOL of FIG. 4 [IOL 60]

The IOL 60 is similar to IOL 61 illustrated in FIGS. 1-3. IOL 60 comprises an optic positioning member 62 wherein the optic positioning member 62 presents an anterior segment 66 and a posterior segment 68 each having a central opening therein 67, 69. A plurality of individually continuous, circumferentially spaced, arcuate in cross-section positioning legs 64 extend from anterior segment 66 and are joined to the margin of optic 32, with openings 71 defined between adjacent pairs of the legs 64, by haptic arms 72. The haptic arms 72 extend between the posterior segment 68 to the margin of the optic 32. The haptic arms 72 join the optic 32 and the optic positioning member 62. This embodiment is similar to IOL 61 in that it may also be constructed with a thin membrane as disclosed in U.S. patent application Ser. No. 09/940,018, filed Aug. 27, 2001 which has been incorporated by reference herein.

In this embodiment, it is important that the posterior segment 68 of the optic positioning member 62 not be fixed with respect to the posterior portion of the capsule 22. This would not be the case if the posterior segment 68 was continuously connected with the positioning legs 64. While not shown in the figures, the anterior segment 66 may be continuously connected by an annular haptic. IOL 60 is implanted and operates in the same manner as IOL 61. The IOL 60 of the present invention typically has a diopter value of from about 16 to 26.

Furthermore, optic positioning member 62 construction is disclosed in previously filed application for U.S. patent Ser. No. 10/280,937 entitled Accommodating Intraocular Lens Implant and U.S. patent Ser. No. 09/940,018 entitled Intraocular Lens Implant Having Eye Accommodating Capabilities both to the same applicant, which are hereby incorporated by reference herein as is necessary for a full and complete understanding of the present invention.

The IOL of FIG. 5 [IOL 60a]

A preferred IOL 60a according to the invention is illustrated in FIG. 5. Similar to the IOL 60 embodiment described above, this IOL 60a comprises an optic 32 and an optic positioning member 74 presenting an anterior segment 66a and a posterior segment 68a. A plurality of circumferentially spaced, arcuate in cross-section positioning legs 76 extend from the anterior segment 66a to the optic 32. The haptic arm 72a extends posteriorly from the anterior segment 66a to the optic 32. In a further preferred embodiment of IOL 60a, the optic 32 may be connected to the optic positioning member 74 via a plurality of haptic arms (not shown). The plurality of haptic arms are disposed at various locations about anterior segment 66a and extend posteriorly towards the optic 32. The plurality of legs 76 are continuously attached to each other through continuous sections 80 presenting annular orifices 82 therethrough. This embodiment is similar to IOL 61 and 60 in that it may also be constructed with a thin membrane as disclosed in U.S. patent application Ser. No. 09/940,018, filed Aug. 27, 2001 which has been incorporated by reference herein.

IOL 60a is implanted and operates in a similar manner to IOLs 61 and 60. The IOL 60a of the present invention typically has a diopter value of from about 16 to 26. Furthermore, the construction of optic positioning member 74 is disclosed in previously filed application for U.S. patent Ser. No. 10/280,937 entitled Accommodating Intraocular Lens Implant and U.S. patent Ser. No. 09/940,018 entitled Intraocular Lens Implant Having Eye Accommodating Capabilities both to the same applicant, which are hereby incorporated by reference herein as is necessary for a full and complete understanding of the present invention.

The IOL of FIG. 6 [IOL 60b]

FIG. 6 depicts yet another preferred IOL 60b according to the invention. This IOL 60b also comprises an optic 32 and an optic positioning member 84 presenting an anterior segment 66b and a posterior segment 68b. The optic positioning member 84 further comprises a plurality of circumferentially spaced, arcuate in cross-section positioning legs 88 having openings 86 therein between adjacent pairs of legs 88. In essence, the IOL 60b is configured in much the same fashion as the IOL 60, with the exception that a plurality of haptic arms 72b extend from equatorial segment 54 toward the optic 32. When the IOL 60b is in its original, non-compressed state, the haptic arms 72b are vaulted slightly toward anterior segment 66b.

This embodiment is similar to IOL 61, 60, and 60a in that it may also be constructed with a thin membrane as disclosed in U.S. patent application Ser. No. 09/940,018, filed Aug. 27, 2001 which has been incorporated by reference herein.

IOL 60b is implanted and operates in a similar manner to IOLs 61, 60 and 60a. The IOL 60b of the present invention typically has a diopter value of from about 16 to 26. Furthermore, the construction of optic positioning member 84 is disclosed in previously filed application for U.S. patent Ser. No. 10/280,937 entitled Accommodating Intraocular Lens Implant and U.S. patent Ser. No. 09/940,018 entitled Intraocular Lens Implant Having Eye Accommodating Capabilities both to the same applicant, which are hereby incorporated by reference herein as is necessary for a full and complete understanding of the present invention.

Figure 8:
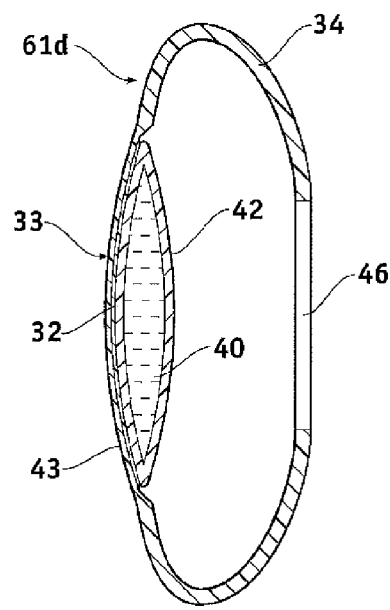
FIG. 8 is a vertical sectional view of the IOL of FIG. 3 showing the optic bonded to the posterior surface of the anterior segment of the IOL of the invention.

The IOL of FIGS. 7 and 8 [IOL 61d]

IOL 61d is another embodiment of the present invention. IOL 61d presents a variation upon the structure of IOL 61 wherein the optic 32 is bound to either the anterior surface 31(a) or the posterior surface 31(b) of the optic positioning member 34. IOL 61d operates in and is implanted in the same manner as IOL 61.

Notably, IOL 61d illustrated in FIGS. 7 and 8 comprises a liquid refractive material 40 enveloped within the capsule 42. The indices of refraction of the wall 43 and the refractive material 40 may be varied to satiate surgical, medical, or manufacturing needs.

Figure 9:
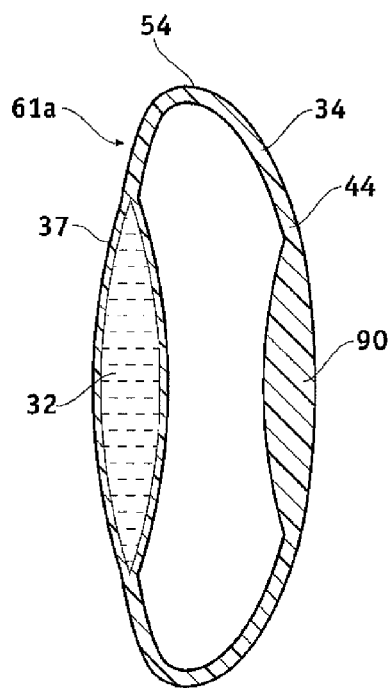
FIG. 9 is a vertical sectional view of another embodiment of the invention showing the optic located at the anterior segment of the IOL and a posterior rigid optic at the posterior segment of the IOL.
Figure 10:
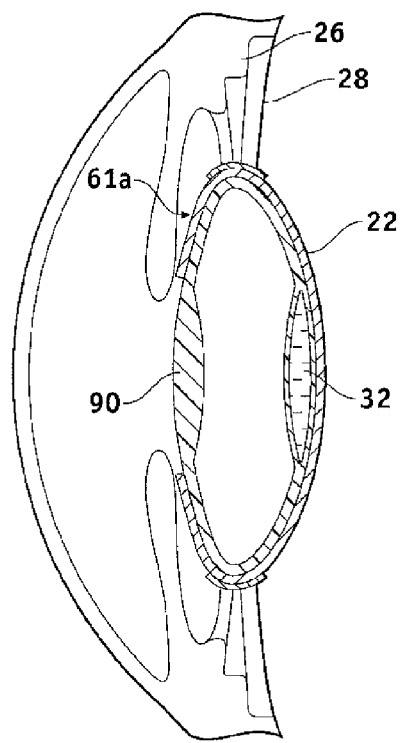
FIG. 10 is a vertical sectional view of the IOL of FIG. 9 positioned within the eye, with the optic located at the posterior segment of the IOL and a rigid optic at the anterior segment.

The IOL of FIGS. 9 and 10 [IOL 61a]

IOL 61a differs from the embodiments discussed thus far in that while the optic 32 is operably coupled to the anterior segment 37 of the optic positioning member, a second rigid optic 90 is operably coupled to the posterior segment 44. The optics 32, 90 are positioned on opposed segments 37, 44 of the optic positioning member such that the optics 32, 90 share the same optical axis. Opposition or opposed in this context is used consistently in this application to mean positioned on the opposite side of equatorial axis 56(a) such that both optics share substantially the same optic axis, and are aligned such that the IOL provides undistorted vision. The posterior optic 90 is made of the same material as the optic positioning member 34, however, one of ordinary skill in the art will recognize that the posterior optic 90 may be constructed of the inventive refractive material as well.

This embodiment is implanted and operates in essentially the same manner as the IOLs discussed thus far, but differs because it includes a second opposed rigid optic 90. The anterior optic 32 converges light upon the posterior optic 90. The posterior optic 90, in turn, diverges the light onto the retina. Any irregularities in the cornea 16 or the natural crystalline lens 24 are counteracted by the highly refractive material 102, thereby bringing the image to focus upon the retina. This embodiment also accommodates in response to ciliary body 26 movement. When the ciliary body 26 contracts, the IOL 61a assumes a spheroid shape. The anterior optic 32 moves anteriorly whereas the posterior optic 90 moves posteriorly. When the ciliary body 26 retracts, the zonules 28 exert a tensional pull upon the IOL to change the IOL to a discoid shape. The anterior optic 32 moves posteriorly whereas the posterior optic 90 moves anteriorly. The IOL 61a of the present invention typically has a diopter value of from about 16 to 26.

IOL 61a may also be positioned within the eye 10 such that the rigid optic 90 is located anteriorly and the optic 32 is positioned posteriorly as illustrated in FIG. 10. When the IOL 61a is positioned within the eye 10 in this manner, the IOL 61 has a combined total refraction of about 16 to 26 diopters.

The IOL of FIGS. 11-15 [IOL 92]

Another preferred embodiment of the present invention includes an anterior optic 94a and a posterior optic surface 96a integral with an optic positioning member 98, such that the IOL 92 presents a unitary structure for implantation within the capsule 22 of the human eye 10. (See FIG. 11) IOL 92 comprises a main body presenting a pre-formed enclosed flexible bag 100 having a resilient fill material 102(a) therein. The pre-formed enclosed flexible bag 100 may also be filled with other refractive media disclosed herein. Flexible bag 100 comprises an anterior segment 104, and a posterior segment 106. Flexible bag further includes wall 112 which, when viewed in cross section, forms and extends radially from an anterior arcuate wall segment 94 and converges upon the posterior segment 106 of the IOL 92 to form an opposing posterior arcuate wall segment 96. The opposing arcuate wall segments 94, 96 define opposed anterior and posterior optic surfaces 94a, 96a when cavity 114 of enclosed flexible bag 100 is filled with material 102(a). Although the terminology 'optic surface' is used herein to describe surfaces 94a and 96a, these surfaces 94a, 96a, operate functionally as optics. Therefore, the term optic may be used interchangeably to describe optic surfaces 94a, 96a within the remainder of this disclosure.

The anterior optic surface 94a and the posterior optic surface 96a have a combined radius of curvature of from about 16 to 26 diopters. (See FIG. 11) The anterior optic surface 94a and the posterior optic surface 96a are both illustrated as convex in shape. When viewed in cross-section, anterior segment 94 and posterior segment 96 are connected by a pair of opposed arcuate equatorial segments 124a as shown in FIG. 14.

Wall 112 includes a fill aperture 118 with a plug therein closing the aperture 118. Although aperture 118 is illustrated at location 120 of the IOL 92, the aperture 118 can be formed at any location on the IOL 92. Preferably the IOL 92 will have an outer equatorial diameter (distance of IOL 92 taken through equatorial axis 124) of from about 8 to 12 mm. (See FIG. 13) Preferably the IOL will have an outside dimension through the central polar axis 122 of from about 2 to 5 mm. (See FIG. 13)

An ophthalmologist fills cavity 114 with material 102(a) prior to surgical implantation of the IOL 92 within the human eye 10 by inserting the material 102(a) through the aperture 118. After cavity 114 is filled, the aperture 118 is sealed. The ophthalmologist removes the natural crystalline lens 24 by conventional methods, leaving an opening in the anterior wall 23(a) of the capsule 22. The IOL 92 is folded an inserted within the capsule 22 through the opening. Implantation of the IOL 92 does not require suturing of the eye 10 be because the instant IOL 92 is capable of being implanted through a small opening in the capsule 22.

IOL 92 operates in the same manner as IOL 61a because IOL 92 includes opposed optic surfaces 94, 96. Anterior optic 94 converges light upon the posterior optic 96, which in turn, diverges light onto the retina. The IOL 92 responds to contraction of the ciliary body 26 by assuming a spheroid shape.

IOL of FIG. 16 [IOL 61]

FIG. 16 illustrates optic 32 of the inventive IOL 61 formed from a resilient silicone gel material. Therefore, the IOL 61 of FIG. 16 does not depict the refractive material enveloped within a pre-formed capsule 42 having a thin continuous wall 43. The capsule 42 is not needed when the refractive material is formed from a resilient, shape-retaining synthetic material such as the silicone gel discussed above.

IOL of FIG. 17 [IOL 61c]

Another preferred embodiment of the present invention includes an optic positioning member 34 operably coupled with two optics 142, 144 to change shape in response to ciliary body 26 movement. IOL 61c includes a resilient optic 142 surrounded by a rigid optic 144. The resilient optic 142 is formed of the refractive material discussed above. The rigid optic 144 is formed of the same material as the optic positioning member 34. Both optics 142, 144 are housed within a pre-formed capsule 42 as described in connection with IOL 61.

IOL 61c operates in a similar manner as the embodiments discussed so far, but differs in that the resilient optic 142 surrounded by the rigid optic 144 maintains a constant volume in response to ciliary body 26 movement. The constant volume of the resilient optic 142 coupled with the relatively high refractive index of the refractive material contained therein confers increased light-bending properties upon the resilient optic 142.

Figure 18:
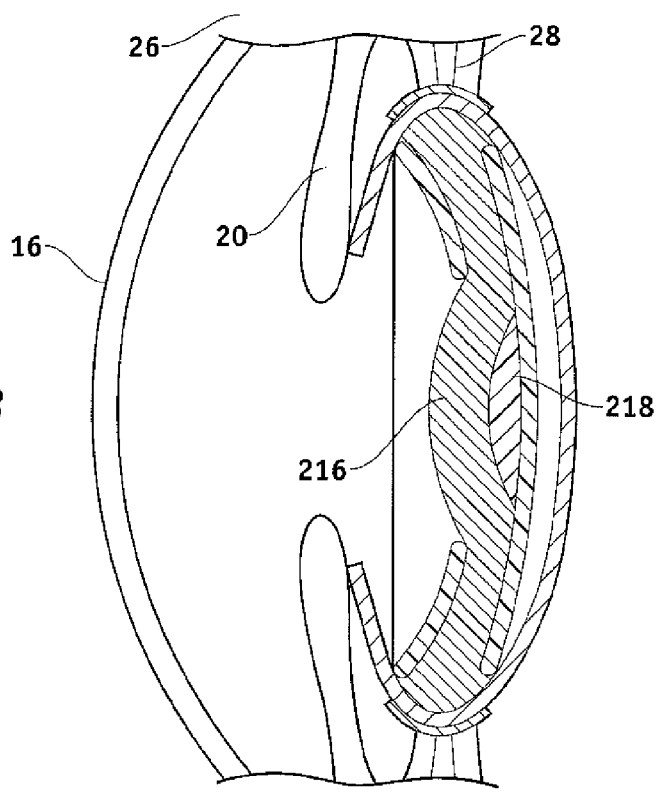
FIG. 18 is a vertical sectional view of another embodiment of the present invention, showing an IOL of the invention within the capsule of an eye, with the eye focused on an object located at a distance from the viewer.
Figure 19:
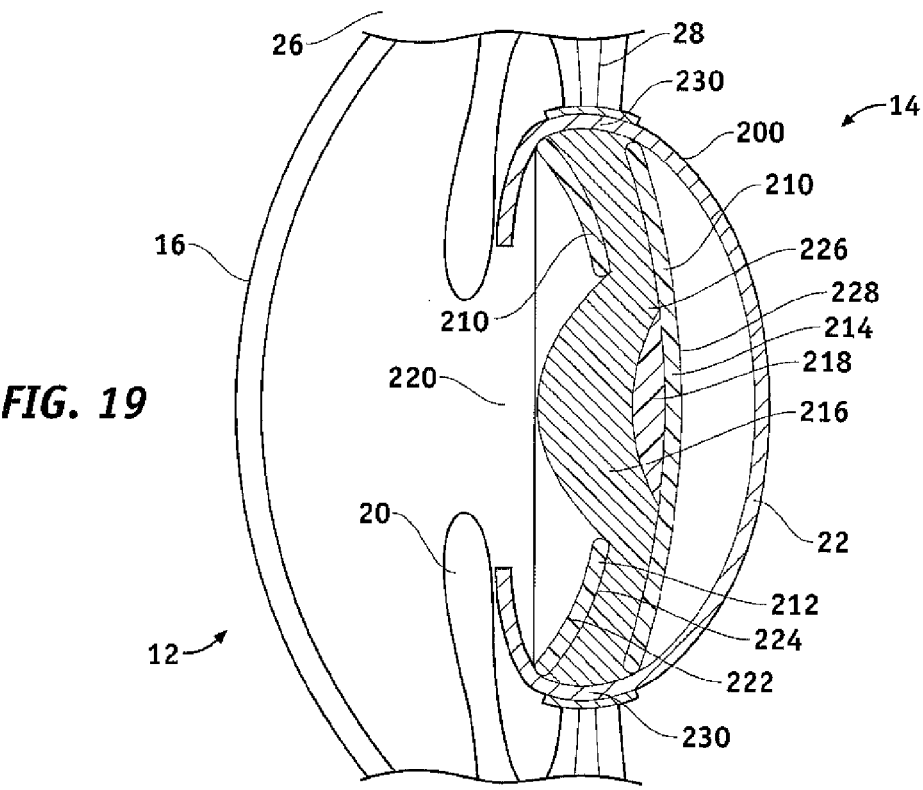
FIG. 19 is a view similar to that of FIG. 18, but illustrating the IOL in an accommodated position owing to contraction of the ciliary muscle.

IOL of FIGS. 18 and 19 [IOL 200]

Another preferred embodiment is an IOL 200 having an annular optic positioning member 210 presenting spaced-apart arcuate anterior 212 and posterior segments 214. The IOL 200 further includes an anterior resilient optic 216 and a posterior rigid optic 218 operably coupled to the optic positioning member 210 to change shape in response to ciliary body 26 movement.

The anterior segment 212 of the optic positioning member 210 contains an opening 220 of from about 7 to 3 mm, and more preferably of about 4 mm wide. The anterior segment 212 further includes an outer margin 222 and an inner margin 224. The outer margin 222 is defined as the anterior portion of the anterior segment 212, or that portion of the segment 212 closest to the iris 20. The posterior segment 214 also includes an inner margin 226 and an outer margin 228 wherein the inner margin 226 of the posterior segment 214 is the margin closest to the iris 20 as well. The space between the anterior segment 212 and the posterior segment 214 is occupied by refractive material such that the refractive material is adjacent to the inner margins 224, 226 of the segments 212, 214. The refractive material protrudes beyond the outer margin 222 of the anterior segment 212. This protrusion defines the resilient optic 216. The refractive material used herein is the refractive silicone gel discussed above. The silicone gel refractive material may be pre-formed into the desired shape and connected, by posts, to the segments 212, 214 of the optic positioning member 210. The refractive material may also be encompassed within a bladder which is also similarly connected to the segments 212, 214. In this case, the refractive material used may also be a liquid.

The IOL 200 may further include a second rigid optic 218 opposed to resilient optic 216. The rigid optic 218 is made of the same material as the optic positioning member 210 and is supported by the posterior segment 214. As mentioned above, the space between the segments 212, 214 is occupied by refractive material. This IOL 200 differs from the other embodiments discussed herein because the refractive material is not completely contained by the optic positioning member 210 in addition to the optic 216 defining protrusion which extends beyond the outer margin 222 of the anterior segment 212. The refractive material is positioned between the two segments 212, 214 such that the refractive material comes into direct contact with the biological capsule 22 at locations 230.

IOL 200 is implanted in the same manner as IOL 61 after IOL 200 is assembled, and operates in a similar manner to the other IOLs having opposed optics discussed herein. Contraction of the ciliary body 26 and subsequent relaxation of the zonules 28 exerts force upon the refractive material causing the material to protrude outward to extend beyond the outer margin 222 of the anterior segment 212. When the ciliary body 26 retracts, the zonules 28 exert a tensional pull upon the capsule 22, and the refractive material assumes its more flattened shape to view objects located at a distance.

IOL of FIGS. 20 and 21 [IOL 61b]

The IOL 61b illustrated in FIGS. 20 and 21 demonstrate yet another preferred embodiment of the invention. FIGS. 20 and 21 demonstrate any of the IOLs of FIGS. 1-8 and 16 discussed above positioned within the eye 10 such that the optic 32 is positioned posteriorly. One of skill in the art would readily appreciate that although FIGS. 20 and 21 illustrate any of the IOLs of FIGS. 1-8 and 16 in the vertical sectional view, any of the IOLs of the present invention may be positioned such that the anterior optic faces posteriorly. FIG. 20 illustrates the IOL of the present invention in the accommodated shape. FIG. 21 illustrates the IOL in the disaccommodated shape.

IOL of FIG. 22 [IOL 61e]

IOL 61e illustrated in FIG. 22 is similar to IOL 61c illustrated in FIG. 17. IOL 61e differs from IOL 61c in that the resilient optic 142a surrounds the rigid optic 144a. FIG. 22 illustrates IOL 61e positioned posteriorly in the capsule 22 of the eye 10. The resilient optic 142a changes shape in response to ciliary body 26 movement. The change in curvature of the resilient optic 142a provides about 3 diopters of convergence while the rigid optic 144a essentially maintains its shape.

Although the invention has been described with reference to the preferred embodiment illustrated in the attached drawing figures, it is noted that equivalents may be employed and substitutions made herein without departing from the scope of the invention as recited in the claims. For example, the IOLs of the present invention may all be constructed in the disaccommodated or accommodated shapes. Also, while the foregoing method of inserting the IOL in the capsule 22 presumed that a portion of the anterior wall 23(a) of the capsule 22 would be removed with the natural crystalline lens 24, it will be appreciated that it may be possible to insert the IOL an incision in the posterior wall 53 of the capsule 22. Furthermore, while the foregoing description discloses that the IOL could be utilized to correct refractive error, the IOL may be used in any situation where the natural crystalline lens 24 should be replaced. For example, the IOL may be used to correct myopia, hyperopia, presbyopia, cataracts, or a combination thereof. Various refractive media may be used to fill cavity 114 of IOL depending upon the desired index of refraction.

What is claimed:

1. An accommodating intraocular lens (IOL), comprising: an anterior, resilient optic disposed about an optical axis; a posterior, rigid optic disposed about the optical axis, the rigid optic being less resilient than the resilient optic; an optic positioning member comprising a plurality of arcuate in cross-section positioning legs, each positioning leg with an equatorial segment disposed along an equatorial plane and configured to conform with an inner surface of an equatorial portion of a capsule of an eye, each positioning leg including anterior and posterior segments disposed on opposite sides of the equatorial segment, each anterior segment being coupled to the resilient optic by a haptic arm extending posteriorly from the anterior segment to the periphery of the resilient optic and each posterior segment being coupled to the periphery of the rigid optic; wherein the plurality of positioning legs are circumferentially spaced around the resilient optic and rigid optic forming a generally annular shape; and wherein, in response to ciliary body movement of an eye, the resilient optic and the rigid optic move in opposite directions from one another along the optical axis, wherein the positioning member is operable for changing the radius of curvature of the resilient optic in response to ciliary body movement so as to affect the refractive power of the resilient optic, wherein the positioning legs and the optics cooperatively present a spheroid shape, and wherein the resilient optic comprises a gel material enveloped within a pre-formed capsule having a thin continuous wall.

2. The intraocular lens of claim 1, wherein the resilient and the rigid optic are made of the same material as the optic positioning member.

3. The intraocular lens of claim 1, wherein the resilient optic or the rigid optic is made of the same material as the optic positioning member.

4. The intraocular lens of claim 1, wherein the resilient optic or the rigid optic comprises a resilient silicone gel material.

* * * * *